United States Patent
Willis et al.

(10) Patent No.: US 6,916,307 B2
(45) Date of Patent: Jul. 12, 2005

(54) CATHETER WITH DISTALLY DISTENDING BALLOON

(75) Inventors: Allan F. Willis, Chubuck, ID (US); Kelly J. Christian, Pocatello, ID (US); Mike Kenowski, Pocatello, ID (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 615 days.

(21) Appl. No.: 09/887,279

(22) Filed: Jun. 22, 2001

(65) Prior Publication Data

US 2002/0032407 A1 Mar. 14, 2002

Related U.S. Application Data

(63) Continuation of application No. 09/372,133, filed on Aug. 11, 1999, now Pat. No. 6,264,631, which is a continuation of application No. 09/022,608, filed on Feb. 12, 1998, now Pat. No. 5,997,503.

(51) Int. Cl.[7] .......................................... A61M 29/00
(52) U.S. Cl. ....................... 604/96.01; 604/103.06; 604/103.07; 604/103.08
(58) Field of Search ........................ 604/27, 28, 41, 604/48, 49, 54, 93, 96.01, 99.04, 103.06, 103.07, 103.08, 175, 257, 261, 264, 512, 907, 908, 910, 912, 915, 917, 921, 103.13, 103.09

(56) References Cited

U.S. PATENT DOCUMENTS

| | | | |
|---|---|---|---|
| 2,667,875 A | * | 2/1954 | Frederick ............... 604/103.13 |
| 3,050,066 A | | 8/1962 | Koehn |
| RE29,207 E | | 5/1977 | Bolduc et al. |
| 4,402,307 A | * | 9/1983 | Hanson et al. ................ 600/18 |
| 4,467,790 A | * | 8/1984 | Schiff ........................... 600/18 |
| 4,527,549 A | * | 7/1985 | Gabbay ....................... 600/18 |
| 4,555,242 A | | 11/1985 | Saudagar |
| 4,575,371 A | | 3/1986 | Nordqvist et al. |
| 4,796,629 A | | 1/1989 | Graqzel |
| 4,798,592 A | | 1/1989 | Parks |
| 4,841,981 A | * | 6/1989 | Tanabe et al. .............. 600/505 |
| 4,927,412 A | | 5/1990 | Menasche |
| 4,976,710 A | | 12/1990 | Mackin |
| 5,042,976 A | * | 8/1991 | Ishitsu et al. ............. 604/96.01 |
| 5,074,845 A | | 12/1991 | Miraki et al. |
| 5,160,321 A | * | 11/1992 | Sahota .................. 604/101.03 |
| 5,195,970 A | * | 3/1993 | Gahara .................. 604/103.08 |
| 5,304,340 A | * | 4/1994 | Downey ..................... 264/521 |
| 5,308,325 A | | 5/1994 | Quinn et al. |
| 5,395,333 A | | 3/1995 | Brill |
| 5,441,485 A | | 8/1995 | Peters |
| 5,759,172 A | | 6/1998 | Weber et al. |
| 5,997,503 A | | 12/1999 | Willis et al. |

FOREIGN PATENT DOCUMENTS

JP        6261951 A        9/1994

* cited by examiner

Primary Examiner—Sharon Kennedy
(74) Attorney, Agent, or Firm—Dority & Manning, P.A.

(57) ABSTRACT

A balloon catheter having a balloon disposed upon an elongate shaft near a relatively rigid distal insertion tip, a fluid lumen for fluid communication with a body cavity and an inflation lumen for fluid communication with the balloon. The balloon holds the catheter tip within a body cavity such as the stomach for long-term enteral feeding. The balloon is configured such that upon inflation, the balloon distends distally to cover the distal tip thus insulating it from sensitive anatomy.

3 Claims, 3 Drawing Sheets

CATHETER WITH DISTALLY DISTENDING BALLOON

This application is a continuation of U.S. patent application Ser. No. 09/372,133, filed Aug. 11, 1999 now U.S. Pat. No. 6,264,631, which is a continuation of U.S. patent application Ser. No. 09/022,608, filed Feb. 12, 1998, now U.S. Pat. No. 5,997,503.

FIELD OF THE INVENTION

The present invention relates generally to an apparatus for catheterizing a body cavity, and is particularly directed to a balloon catheter with a distally distending balloon which envelops the catheter tip upon inflation.

DESCRIPTION OF THE RELATED ART AND BACKGROUND OF THE INVENTION

Catheterizing a body cavity can be advantageous in many instances such as to insert or remove fluids to or from the cavity. It is also known to be desirable to use a device such as an inflated balloon near the tip of the catheter to hold it in the body cavity. This type of balloon is fashioned around the perimeter of the catheter shaft such that when it is deflated, it adds little to the overall diameter of the catheter. When the catheter tip is inside the body cavity, the balloon is inflated and thereby precludes withdrawal of the portion of the catheter distal to and covered by the balloon. Examples of cavities often catheterized in this manner are the stomach or an intestine. Example of the function of such catheterization are fluid drainage and bolus feeding.

Attachment of the balloon to the catheter shaft is commonly accomplished by gluing proximal and distal cuffs to corresponding positions on the external surface of the catheter shaft. Such balloon cuffs are longitudinal sections of the balloon whose inside diameter correspond to the outside diameter of the shaft at positions near the distal tip of the catheter and have a distance between which is roughly the length of the uninflated balloon from the distal tip. It will be appreciated that the size of the catheter and the uninflated length of the balloon will vary in accordance with the size and shape of the body cavity and the nature of the matter to be moved through the catheter. The glue cuffs must be of sufficient length to provide a tight and durable seal between the balloon and the catheter shaft.

As the uninflated balloon is inherently elastic, the catheter shaft must be rigid enough to withstand insertion pressures. This is especially true at the distal catheter tip of the shaft.

The volume and internal geometry of hollow internal body organs is often dynamic. A clear example of this is the stomach. Opposing internal surfaces and folds regularly come into contact with each other. This is especially true when the cavity is empty and the animal is physically active. The presence of a stiff catheter tip in this environment, has been suspected of irritating the opposing surfaces of the body cavity.

Accordingly, there is a need in the art for a balloon catheter with a stiff distal tip isolated from opposing internal body cavity surfaces.

OBJECT AND SUMMARY OF THE INVENTION

It is, therefore, an object of the present invention to provide a balloon catheter whose inflated balloon isolates a portion of the distal tip and thereby protects opposing internal cavity surfaces from irritation.

It is a further object of the present invention to provide such a balloon catheter whose uninflated balloon does not interfere with the catheter distal tip upon insertion.

These objects are generally accomplished by an inventive balloon catheter having a stiff distal tip to aide insertion of the catheter through a stoma or other opening to a body cavity. Immediately proximal to the tip is a shaft, and disposed upon the shaft in coaxial relationship is a balloon. Upon inflation of the balloon through an inflation lumen in the shaft, the distal end of the balloon distends over the stiff tip to protect an opposing wall of the body cavity in which the tip, balloon, and part of the shaft are located. The distal end of the inflated balloon has much greater surface area and is more resilient than the distal tip. The balloon thus, shields the opposing wall from the potential irritation which could possibly be caused by the stiff distal tip.

The general advantages obtained by this inventive catheter can be specifically brought about by a first preferred embodiment in which a plurality of annular rings are disposed about the proximal end of the balloon. These rings force a greater volume of inflation medium into the distal end of the balloon, thus urging it to distend in the direction of the tip. The first preferred embodiment further discloses an annular ring adjacent to a distal glue cuff. The ring provides an initially surmountable radial and proximal bias upon the distal portion of the balloon. When the balloon is inflated further, the distal ring inverts or transposes in radial orientation to the shaft, thereby distending the balloon over a portion of the shaft distal to the previously uninflated balloon and biasing a portion of the balloon radially toward the distal tip.

In a second preferred embodiment, a plurality of centrally located annular rings bias radially against inflation of the balloon. These forces cause the balloon to distend longitudinally. The proximal distention is limited by the proximal body cavity wall. Thus, the distention over the distal tip is even more pronounced.

In a third preferred embodiment, the uninflated balloon is longer than the portion of the shaft to which it is glued. This creates a longitudinal excess that allows the balloon to overlap the glue cuffs and distend longitudinally upon inflation. As in the previously described embodiment, the proximal wall enhances distal distention of the balloon.

In a fourth preferred embodiment, the balloon has a thicker portion at the proximal end and a thinner portion at the distal end. The natural bias of the balloon adjacent the proximal glue cuff urges the bulk of the inflation to occur adjacent the distal glue cuff where the natural bias is relatively weak.

These and other features and advantages will be seen from the following detailed description of the presently preferred embodiments and from the claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF THE PREFERRED EMBODIMENT OF THE PRESENT INVENTION

Figure 1:
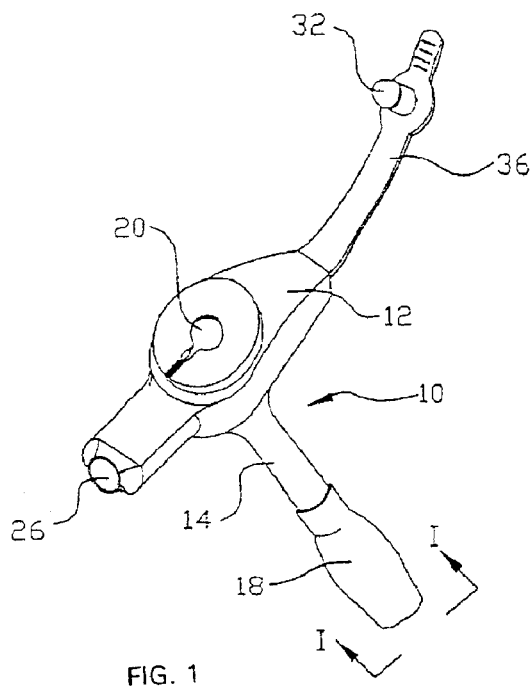
FIG. 1 is a perspective view of a first preferred embodiment of a balloon catheter made in accordance with the present invention having an uninflated balloon.
Figure 2:
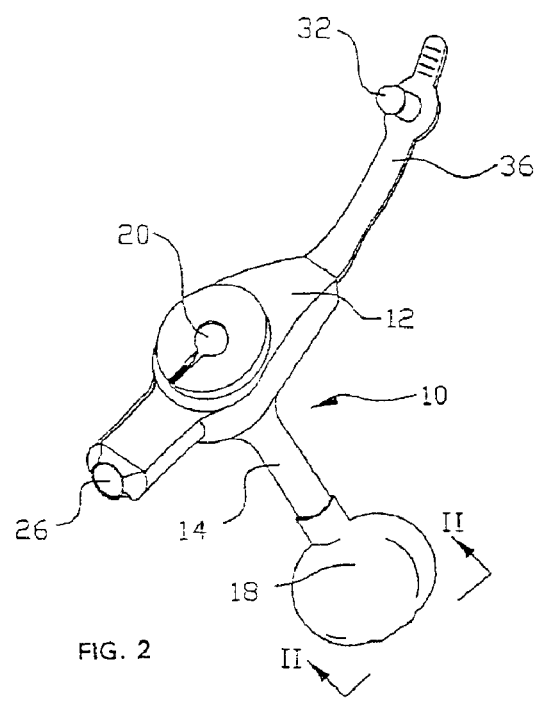
FIG. 2 is a perspective view of a first preferred embodiment of the balloon catheter of FIG. 1 with the balloon inflated.

Reference will now be made to the drawings wherein like structures will be provided with like reference numerals.

Referring now to FIGS. 1–5, there is shown, generally designated at 10, a balloon catheter. The balloon is comprised primarily of a proximal head 12, a shaft 14 and a balloon 18. The head further comprises a proximal opening 20 to a feeding lumen 22 within the shaft 14, for feeding bolus or other nutrient formula (not depicted) to a patient (not depicted). Disposed between the opening 20 and the lumen 22, is an anti reflux valve 24 to prevent back-flow of the nutrient formula. Inflation port 26 is also disposed in head 12. Inflation port 26 communicates with inflation lumen 28 which extends longitudinally through the shaft 14. The inflation lumen 28 terminates laterally to the shaft 14 at port 34, inside the balloon 18. A releasable one-way fluid valve 30 is disposed between the inflation port 26 and inflation lumen 28. Application of positive fluid pressure such as air or saline, within the upon the and inflation lumen 28 by way of the inflation port 26, causes the balloon to inflate. One-way fluid valve 30 prevents inadvertent deflation of the balloon 18. Also associated with the head 12, is a plug 32 for the proximal opening 20, and a lanyard 36 for retaining the plug in a ready position. Thus, the plug can be inserted in lumen 20 thereby precluding contamination when said lumen is not in use. Feeding lumen 22 extends longitudinally through shaft 14 and terminates at the distal tip 40 of the shaft.

The various components of balloon catheter 10 are formed from bio-compatible materials such as medical grade silicone, with the possible exception of valves 24 and 30, which are formed of a suitable polymer such a polycarbonate.

The distal tip 40 is comprised of a stiffer material such as silicone, which is suitable for insertion through a body opening, such as a stoma (not depicted). It will be appreciated that tip 40 and shaft 14 must withstand insertion pressures without binding or buckling.

Figure 5:
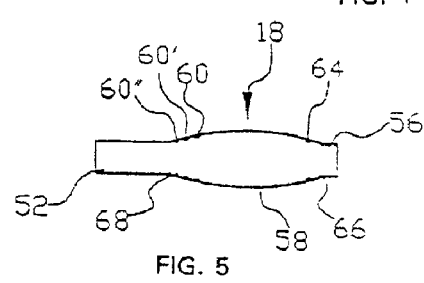
FIG. 5 is a side cross-sectional view of the balloon of FIG. 1 about the longitudinal midline A—A of FIG. 1.

Balloon 18 is more precisely depicted in cross section in FIG. 5. The balloon is essentially comprised of a proximal glue cuff 52 of approximately 5 mm in length, a distal glue cuff 56 approximately 1 mm in length, and an inflatable length 58 therebetween. The proximal cuff 52 is glued to the outside of shaft 14 proximal to inflation lumen port 34. Distal glue cuff 56 is glued to an annulus of the tip 40 of shaft 14, such that the port 34 exits lumen 28 between glue cuffs 52 and 56. This provides a fluid-tight enclosure bounded on the periphery by the balloon 18.

Figure 3:
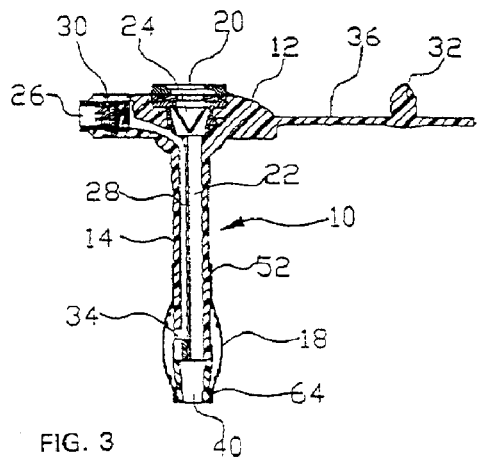
FIG. 3 is a cross-section of the balloon catheter of FIG. 1 about longitudinal midline line I—I.
Figure 4:
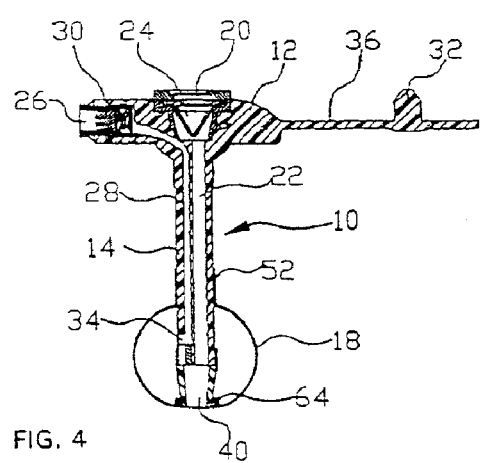
FIG. 4 is a cross section of the balloon catheter of FIG. 2 about longitudinal midline line II—II.

Referring now specifically to FIGS. 3–5, the balloon further comprises a plurality of annular rings 60–64. Annular rings 60, 60', and 60" are disposed in the proximal one half of the balloon and annular ring 64 is disposed adjacent distal glue cuff 56. Each ring 60–64 completely circumscribes balloon 18, and is formulated as an integral molded component of balloon 18. Annular rings 60–64 are approximately double the thickness of the balloon. The most distal proximal ring 60 and the distal ring 64, are approximately 0.2 mm in length and rings 60' and 60 are approximately 0.15 mm 0.01 mm respectively. Balloon 18 further comprises scribe lines 66 and 68 for reference in positioning and gluing cuffs 52 and 56.

Proximal rings 60–60" function to cause a substantial inflation fluid distribution from the proximal longitudinal half to the distal longitudinal half of balloon 18. This is accomplished by a substantially greater radial resistance to inflation exerted by rings 60–60". This resistance is significantly greater than the pressure caused by ring 64. Because rings 60–60" are more numerous and rings 60–60' are substantially further from glue cuff 52 than ring 64 is from glue cuff 56. Eventually, upon increasing inflation, ring 64 reaches a point at which the distal inflation pressure of the balloon 18 overcomes the radial resistance of ring 64. When this happens, ring 64 transposes in radial orientation to shaft 14. This transposition increases the inflation volume of the balloon and distends the distal portion of the balloon 18 over a portion of the rigid distal tip 40, thus protecting physiological structure which may come in contact with tip 40, from irritation. Ring 64 persists in biasing the balloon in axial and distal directions until balloon 18 is deflated.

Figure 6:
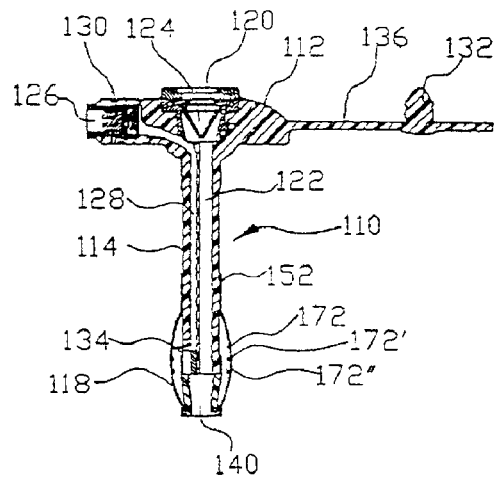
FIG. 6 is a cross-sectional view about a longitudinal midline, of a second embodiment of a balloon catheter having an uninflated balloon.
Figure 7:
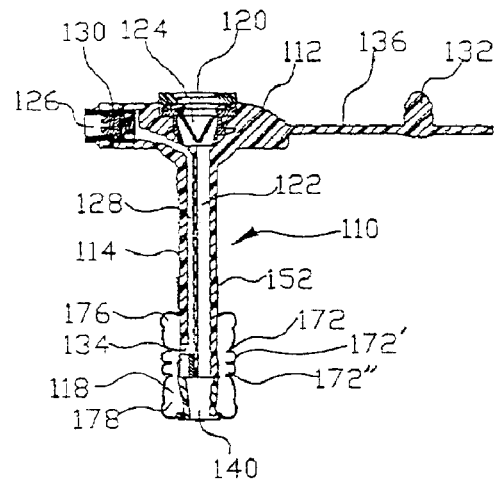
FIG. 7 is a cross-sectional view about a longitudinal midline, of the balloon catheter of FIG. 6, having an inflated balloon.
Figure 8:
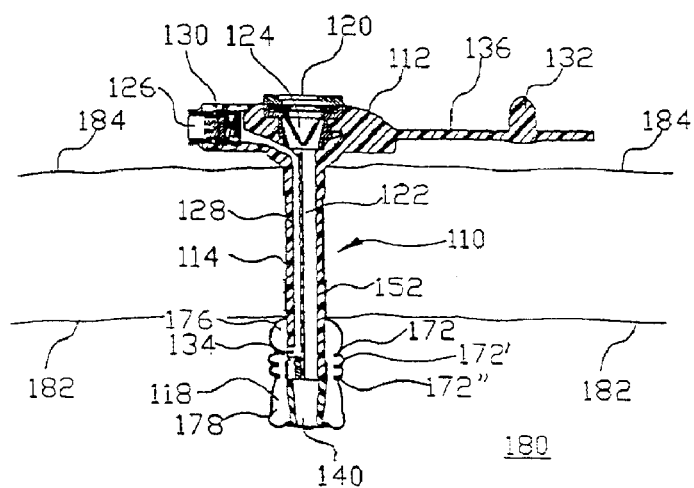
FIG. 8 is the balloon catheter of FIG. 7, further depicting the catheter as is may be placed in a human stomach.

Referring now to FIGS. 6–8 wherein like numerals depict like structure, where applicable, plus one-hundred, relative to the descriptions to FIGS. 1–5. Structure 110–140 is identical to structure 10–40 of FIGS. 1–4, with the exception of balloons 18 and 118 respectively. Balloon 118 has thereabout three annular rings 172, 172' and 172" which are similar in production and mode to rings 60–64 of FIGS. 1–5, except that rings 172–172" are disposed longitudinally central to balloon 118. Rings 172–172" do not invert as does ring 64 of FIGS. 4–5. Rings 172–172" bias the central portion of balloon 118 radially inward upon inflation causing a substantial portion of the volume of an inflation liquid to divert longitudinally as is depicted in FIG. 7. This creates annular proximal 176 and distal 178 lobes in the inflated balloon 118 (FIG. 7).

As is further depicted in FIG. 8, the catheter tip 140 and balloon portion 118 are enclosed within a body cavity 180 comprised by a cavity wall 182. The proximal head 112 is disposed external to the animal or human and the underside of head 112 rests on the skin 184 of the animal (not numbered). If the length of shaft 114 between the proximal end of balloon 118 and the head 112 is properly sized, the skin 184 places the central portion of shaft 114 in tension, and causes cavity wall 182 to exert pressure upon the proximal lobe 176 of balloon 118. Thus, the volume of proximal lobe 176 is shifted to the distal lobe 178, further distending balloon 118 over tip 140 and protecting an opposing portion of cavity wall 182 (not depicted) from possible irritation.

Figure 9:
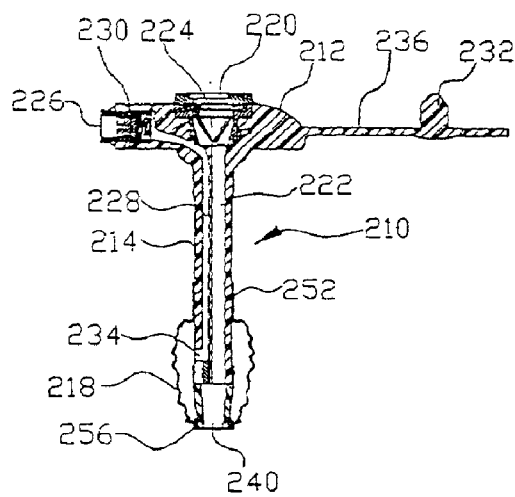
FIG. 9 is a cross-sectional view about a longitudinal midline, of a third preferred embodiment of a balloon catheter having an uninflated balloon.
Figure 10:
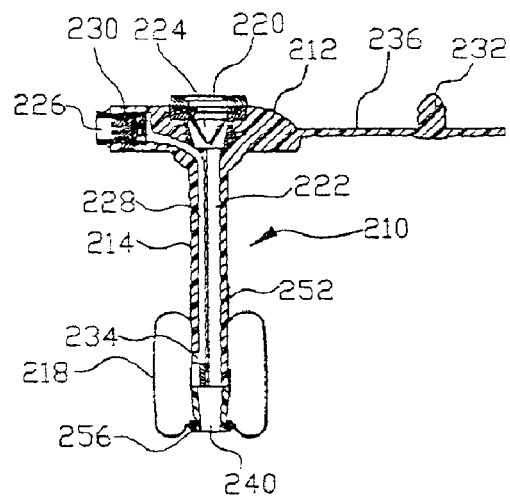
FIG. 10 is a cross-sectional view about a longitudinal midline, of the balloon catheter of FIG. 9, having an inflated balloon.

Referring now to FIGS. 9 and 10 where like numerals depict like structure, where applicable, plus two-hundred, relative to the descriptions to FIGS. 1–5. Structure 210–240 is identical to structure 10–40 of FIGS. 1–4, with the exception of balloons 18 and 218 respectively.

Glue cuffs 252 and 256 of balloon 218 are glued to shaft 214 a distance apart that is less than the length of balloon 218 from glue cuff 252 to glue cuff 256. This is accomplished by gluing cuff 252 to shaft 214 in a conventional manner, but such that cuff 256 naturally extends approximately 1 mm beyond tip 240. After the first attachment is cured using conventional methods, the balloon is bunched up or gathered over the shaft 214 until glue cuff 256 is slightly proximal to tip 240. Glue cuff 256 is then glued and cured to shaft 114 at a corresponding position. The gathers in uninflated balloon 118 allow the balloon to distend longitudinally upon inflation. In a manner similar to that described in conjunction with FIG. 8, the proximal longitudinal distention is forced to the distal end and, thus, further envelops the distal tip 240, as is described in conjunction with FIG. 8.

Figure 12:
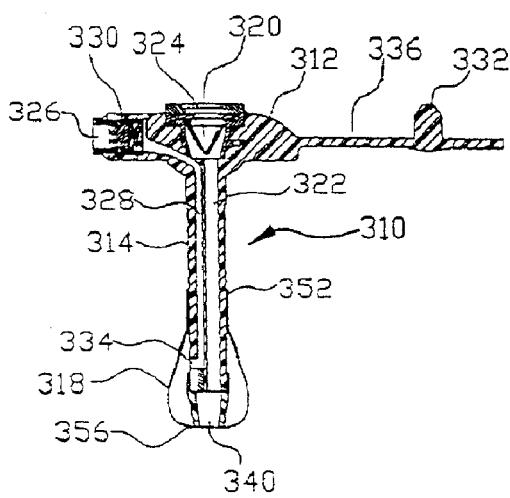
FIG. 12 is a cross-sectional view about a longitudinal midline, of the balloon catheter of FIG. 11, having an inflated balloon.
Figure 11:
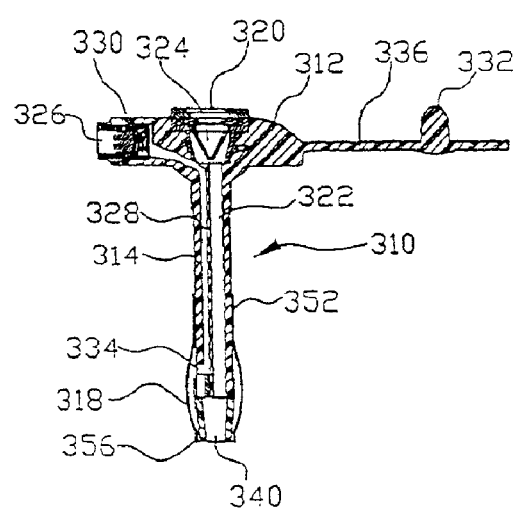
FIG. 11 is a cross-sectional midline, of a fourth preferred embodiment of a balloon catheter having an uninflated balloon.

Referring now to FIGS. 11 and 12 wherein like numerals depict like structure, where applicable, plus three-hundred, relative to the descriptions to FIGS. 1–5. Structure 310–340 is identical to structure 10–40 of FIGS. 1–4, with the exception of balloons 18 and 318 respectively.

Balloon 318 is thicker at its proximal end than it is at its distal end. This can be accomplished by, for example dipping procedures wherein the proximal end stays in the bath for a longer time than the distal end. This accomplishes an even gradient through the entire balloon length. The presently preferred mode leaves a thickness of 0.05 mm at the extreme distal tip and a 0.025 mm thickness at the extreme proximal balloon tip. Thus, the inward radial bias of the balloon immediately adjacent the proximal balloon cuff 352, is greater, because the elastic material comprising the balloon is relatively thickest there. On the other hand, the balloon is thinnest (excluding the portion glued to the shaft) immediately adjacent distal glue cuff 356. Consequently, as balloon 318 is inflated, the proximal portion exerts a greater radial pressure, and the distal portion is distended in a distal direction over tip 340.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modification and arrangements.

What is claimed is:

1. A balloon catheter, comprising:

a longitudinal shaft having a lumen in fluid communication with a catheter tip; and a tubular balloon having proximal and distal ends attached to said shaft such that said balloon is coaxially aligned with said shaft, and a plurality of adjacent annular restraining rings formed integrally with the balloon between said proximal and distal ends, said restraining rings being configured to limit radial expansion of said balloon at said restraining rings, while enabling generally uniform circumferential expansion of said balloon on each side of said rings radially beyond the rings when the balloon is inflated;

wherein said balloon is configured such that a proximal lobe is formed when said balloon is inflated that extends in a proximal direction at least partially past the distal most point of a proximal cuff of said balloon.

2. The balloon catheter of claim 1, wherein a plurality of said restraining rings are disposed at a central portion of said balloon, so as to form proximal and distal lobes when said balloon is inflated.

3. The balloon catheter of claim 1, wherein said restraining rings are spaced apart.

* * * * *